United States Patent [19]

Irick, Jr. et al.

[11] 4,159,270

[45] Jun. 26, 1979

[54] BICHROMOPHORIC BENZOTRIAZOLE-STYRENE ULTRAVIOLET STABILIZERS

[75] Inventors: Gether Irick, Jr.; Charles A. Kelly, both of Kingsport; James C. Martin, Johnson City, all of Tenn.

[73] Assignee: Eastman Kodak Company, Rochester, N.Y.

[21] Appl. No.: 857,732

[22] Filed: Dec. 5, 1977

Related U.S. Application Data

[62] Division of Ser. No. 715,016, Aug. 16, 1976, Pat. No. 4,070,337.

[51] Int. Cl.$^2$ ............................................ C07D 249/20
[52] U.S. Cl. ................................................... 260/308 B
[58] Field of Search ...................................... 260/308 B

[56] References Cited

U.S. PATENT DOCUMENTS

| | | | |
|---|---|---|---|
| 3,766,205 | 10/1973 | Heller | 260/308 B |
| 3,981,884 | 9/1976 | Wang et al. | 260/308 B |

*Primary Examiner*—Paul M. Coughlan, Jr.
*Attorney, Agent, or Firm*—Clyde L. Tootle; Daniel B. Reece, III

[57] ABSTRACT

The invention relates to bichromophoric benzotriazole-styrene compounds which have been found to be effective ultraviolet stabilizers. The invention also relates to ultraviolet degradable organic compositions containing a stabilizing amount of the bichromophoric composition to prevent such degradation. These stabilizers are effective in the presence of other additives commonly employed in polymeric compositions including, for example, pigments, colorants, fillers, reinforcing agents and the like. These ultraviolet stablizers may also be incorporated into the organic compositions in the polymer melt or dissolved in the polymer dope, coated on the exterior of the molded article, film or extruded fiber.

60 Claims, No Drawings

BICHROMOPHORIC BENZOTRIAZOLE-STYRENE ULTRAVIOLET STABILIZERS

This application is a divisional application of Ser. No. 715,016, filed Aug. 16, 1976, now U.S. Pat. No. 4,070,337 which issued Jan. 24, 1978.

This invention relates to bichromophoric benzotriazole-styrene ultraviolet stabilizers and their use in organic compositions. More particularly, the invention relates to bichromophoric benzotriazole-styrene compositions and the stabilization of ultraviolet degradable organic compositions against deterioration resulting from the exposure to such radiations with such bichromophoric compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions is polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb ultraviolet radiation within the band of 2900 to 4000 Å. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

It is still another object of the present invention to provide compositions containing bichromophoric benzotriazole-styrene compositions which are resistant to ultraviolet degradation.

It is a still further object of this invention to provide processes for improving the resistance of organic materials to deterioration and degradation by actinic radiation and especially ultraviolet radiation.

It is a still further object of this invention to provide compositions and processes for improving the resistance of organic materials to deterioration and degradation by actinic radiations, including short wave-length visible radiations.

Further objects and advantages of the invention will be apparent to those skilled in the art from the accompanying disclosure and claims.

In accordance with the present invention, bichromophoric compositions are provided which are useful as ultraviolet stabilizers or ultraviolet screening agents. These organic compositions contain at least one benzotriazole group containing composition connected to a styrene group. The compositions of the present invention have the following structure:

A—B—C wherein A is a group having the structure

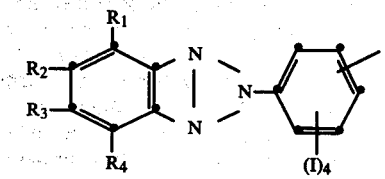

wherein $R_1$, $R_2$, $R_3$ and $R_4$ are hydrogen, lower alkyl or substituted lower alkyl having 1 to 12 carbon atoms, cycloalkyl, substituted cycloalkyl, aryl or substituted aryl having 6 to 18 carbon atoms, lower alkylaryl, aryl-substituted-aryl, chloro, bromo, alkoxy, substituted amino, cyano, carboalkoxy and the substituents $R_1$ and $R_2$, $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$.

I is a substituent listed above for $R_1$, $R_2$, $R_3$ and $R_4$ and is present on all positions of the benzenoid ring, except the carbon atom attached to the N substituent and the carbon atom attached to the B group. The B connecting group is attached to the benzenoid ring in the ortho, meta or para position from the carbon atom connected to the heterocyclic ring. The I substituents can all be one of the substituents listed above or different listed substituents;

wherein

B is a linking group connecting A and C and can be carbonyloxy, oxycarbonylalkyleneoxy, alkyleneoxycarbonyloxy, oxyalkylenecarbonyloxy, oxycarbonyloxy, alkyleneoxy, alkyleneoxyalkyleneoxy, oxyalkylenearylenealkyleneoxy, thio, thioalkyleneoxy, oxy(alkoxy)phosphinooxy, aminocarbonylalkyleneoxy, N-alkylaminocarbonylalkyleneoxy, N-arylaminocarbonylalkyleneoxy, aminocarbonylamino, N-alkylaminocarbonylamino, N-alkylamino, N-arylamino, N-alkylaminoalkyleneoxy, N-arylaminoalkyleneoxy, oxyalkyleneoxy, and oxyaryleneoxy; and C is a group having the formula

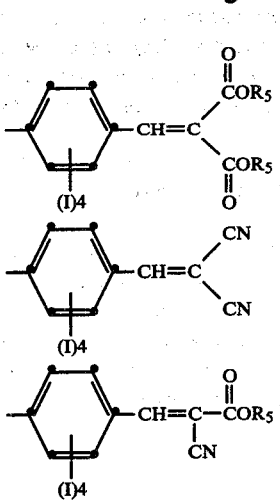

I is the same substituent as listed above and is present in all positions of the benzenoid rings except the carbon atom attached to the B group connecting the A and C moieties. The B connecting group is attached to the benzenoid ring of C in the meta or para position. The I substituents can all be one of the substituents listed above or different listed substituents, and $R_5$ is an alkyl group containing 1 to 20 carbon atoms or a hydroxyalkyl group or a substituted alkoxyalkyl group containing 1 to 20 carbon atoms.

Suitable A groups having the structure

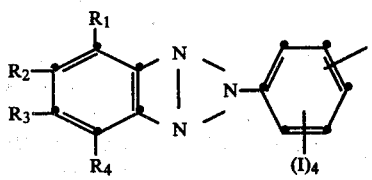

are for example substituted and unsubstituted benzotriazoles such as 4-(5-chloro-2H-benzotriazol-2-yl)phenyl, 4-(2H-benzotriazol-2yl)phenyl, 4-(5-methoxy-2H-benzotriazol-2-yl)phenyl, 2,6-dimethyl-4-(2H-benzotriazol-2-yl)phenyl, 2,6-dimethyl-4-(5-chloro-2H-benzotriazol-2-yl)phenyl, 2-methyl-4-(2H-benzotriazol-2-yl)phenyl, 2-methyl-4-(5-chloro-2H-benzotriazol-2-yl)phenyl, 2-chloro-4-(2H-benzotriazol-2-yl)phenyl, 2,6-dichloro-4-(2H-benzotriazol-2-yl)phenyl, 2-chloro-4-(5-chloro-2H-benzotriazol-2-yl)phenyl, 2,6-dichloro-4-(5-chloro-2H-benzotriazol-2-yl)phenyl, 2,6-dimethyl-4-(5-methoxy-2H-benzotriazol-2-yl)phenyl, 2,6-dichloro-4-(5-methoxy-2H-benzotriazol-2-yl)phenyl, 2-chloro-4-(5-methoxy-2H-benzotriazol-2-yl)phenyl, 2-methyl-4-(5-methoxy-2H-benzotriazol-2-yl)phenyl, 2-phenyl-4-(2H-benzotriazol-2-yl)phenyl, 2-phenyl-4-(5-chloro-2H-benzotriazol-2-yl)phenyl, 2-phenyl-4-(5-benzotriazol-2-yl)phenyl, and the like.

Suitable B groups are for example carbonyloxy, oxycarbonylmethyleneoxy, oxycarbonylethyleneoxy, oxycarbonyl-1,4-butanediyloxy, alkyleneoxycarbonyloxy such as methyleneoxycarbonyloxy, ethyleneoxycarbonyloxy, 1,4-butanediyloxycarbonyloxy, 1,5-pentanediyloxycarbonyloxy, oxycarbonyloxy, alkyleneoxy such as methylenoxy, ethyleneoxy, 1,3-propanediyloxy and the like, alkyleneoxyalkyleneoxy such as methyleneoxymethylenoxy, ethyleneoxyethylenoxy, methyleneoxyethyleneoxy, ethyleneoxymethyleneoxy and the like, oxyalkyleneoxy such as oxymethyleneoxy, oxyethyleneoxy, oxy-1,4-butanediyloxy and the like, oxyalkylenearylenealkyleneoxy such as oxymethylenephenylenemethyleneoxy, oxyethylenephenylenemethyleneoxy, oxypropylenephenylenemethyleneoxy, oxyethylenenaphthylene-ethyleneoxy and the like, thio, thioalkyleneoxy such as thiomethyleneoxy, thioethyleneoxy and the like, oxy(alkoxy)phosphinooxy such as oxy(methoxy)phosphinooxy, oxy(ethoxy)phosphinooxy, oxy(butoxy)phosphinooxy and the like, aminocarbonylalkyleneoxy such as aminocarbonylmethyleneoxy, aminocarbonyl-1,4-butanediyloxy, N-methylaminocarbonylmethyleneoxy, N-phenylaminocarbonylethyleneoxy and the like, aminocarbonylamino, alkylaminocarbonylamino such as N-methylaminocarbonylamino, N-ethylaminocarbonylamino and the like, arylaminocarbonylamino such as N-phenylaminocarbonylamino, N-(3-methylphenyl)aminocarbonylamino, N-arylaminocarbonyl-N'-arylamino, such as N-phenylaminocarbonyl-N'-phenylamino, N-alkylaminocarbonyl-N'-arylamino such as N-methylaminocarbonyl-N'-phenylamino and the like, N-arylaminocarbonyl-N'-alkylamino such as N-phenylaminocarbonyl-N'-methylamino or N-methylaminocarbonyl-N'-phenylamino and the like, alkyleneamino such as methyleneamino, 1,4-butanediylamino, 1,5-pentanediylamino, and the like, aryleneamino such as phenyleneamino and the like, N-alkylaminoalkyleneoxy such as N-methylaminomethyleneoxy, N-ethylaminomethyleneoxy and the like, N-arylaminoalkyleneoxy such as N-phenylaminomethyleneoxy, N-phenylaminoethyleneoxy and the like, oxyalkyleneaminoalkyleneoxy such as oxymethyleneaminomethyleneoxy, oxymethyleneaminoethyleneoxy and the like, alkyleneaminocarbonylamino such as methyleneaminocarbonylamino, ethyleneaminocarbonylamino and the like, oxyalkylene(N-alkyl)aminoalkyleneoxy such as oxymethylene(N-methyl)aminomethyleneoxy and the like;

wherein C is a styrenic group having the formula

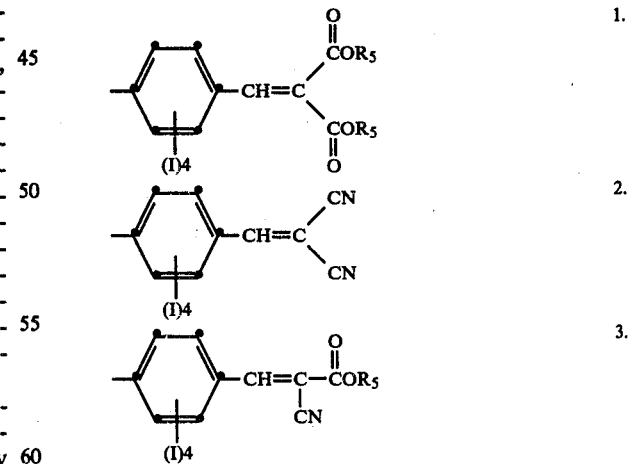

are for example 4-($\beta,\beta$-dicarbomethoxyvinyl)phenyl, 4-[$\beta,\beta$-dicarbo-(2-ethylhexyloxy)vinyl]phenyl, 4-$\beta,\beta$-dicarbo(n-dodecyloxy)vinyl]phenyl, 2-chloro-4-($\beta,\beta$-dicarbomethoxyvinyl)phenyl, 2-methyl-4-($\beta,\beta$-dicarbo-n-butoxyvinyl)phenyl, 2-methoxy-4-($\beta,\beta$-dicarbo-n-butoxyvinyl)phenyl, 2-acetamido-4-($\beta,\beta$-dicarboethoxyvinyl)phenyl, 2-phenyl-4-[$\beta,\beta$-dicarbo-(2-hydroxyethoxy)vinyl]phenyl, 2-cyclohexyl-4-[β,β-dicarbo-(2-methoxyethoxy)vinyl]phenyl, 2-bromo-4-[β,β-dicarbo-(2-n-butoxyethoxy)vinyl]phenyl, 2-cyano-4-(β,β-dicarbo-n-dodecyloxyvinyl)phenyl, 2-isopropyl-4-(β,β-dicarbomethoxyvinyl)phenyl, 2-n-butyl-4-[β,β-dicarbo-(2-β-methoxyethoxy)-vinyl]phenyl, 2-t-amyl-4-(β,β-dicarbo-isopropyloxyvinyl)phenyl, 4-(β,β-dicyanovinyl)phenyl, 2-methyl-4-(β,β-dicyanovinyl)phenyl, 2-cyano-4-(β,β-dicyanovinyl)phenyl, 2-t-butyl-4-(β,β-dicyanovinyl)phenyl, 2-n-cyclohexyl)-4-(β,β-dicyanovinyl)phenyl, 2-t-octyl-4-(β,β-dicyanovinyl)phenyl, 2-benzamido-4-(β,β-dicyanovinyl)phenyl, 2-n-dodecyloxy-4-(β,β-dicyanovinyl)phenyl, 4-(β-cyano-β-carbomethoxyvinyl)phenyl, 2-cyclopentyl-4-(β-cyano-β-carboethoxyvinyl)phenyl, 2-isopropyl-4-[β-cyano-β-carbo-(2-ethylhexyloxy)vinyl]phenyl, 2-chloro-4-[β-cyano-β-carbo-(2-methoxyethoxy)-vinyl]phenyl, 2-methoxy-4-(β-carbomethoxyvinyl)phenyl.

The bichromophoric benzotriazole-styrene compositions can be added to organic compositions which are susceptible to ultraviolet degradation. Such compositions include, for example, polymeric compositions such as polyester fiber and molding compositions, such as poly(ethylene terephthalate), poly(tetramethylene terephthalate) and the like; polyolefins such as, for example, high, medium and low density polyethylene, polypropylene, polybutene and the like; polyamides such as N-methoxymethyl polyhexamethylene adipamide and the like; polycarbonates; polyvinyl chlorides and copolymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene vinyl acetate copolymers; fluorocarbon resins such as poly(vinylidene fluoride); cellulose ethers such as methyl cellulose; polyvinyl esters such as polyvinyl acetate; polyethylene oxide; polyvinyl acetals; polyformaldehydes; and polyurethanes. Such compositions also include natural and synthetic rubbers, such as polybutadiene, and unsaturated organic compositions such as oils and the like, as well as compositions containing such organic compositions.

The bichromophoric benzotriazole-styrene compositions, as effective ultraviolet stabilizers or screening agents, are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 2%, by weight, of the stabilizer effectively stabilizes cellulose acetate butyrate plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel bichromophoric benzotriazole-styrene ultraviolet stabilizers may be incorporated into organic compositions by melt-blending or may be added onto the surface of an organic plastic material prior to being molded into a suitable object. These materials can also be added to coatings and the like which can be applied to the surface of a molded object.

This invention will be further illustrated by the following examples although it will be understood that these examples are included merely for purposes of illustration and are not intended to limit the scope of the invention.

EXAMPLE 1 o-Nitroaniline (0.5 mole) was diazotized in the usual manner with concentrated hydrochloric acid (120 ml.) and sodium nitrite (0.5 mole). The clear diazonium solution was added slowly to a cold solution (0°–5° C.) of 2,6-dimethylphenol (0.5 mole) in 450 ml. of 10% sodium hydroxide. The mixture was stirred for 1 hour and Compound A filtered out (80% yield). One-tenth mole of Compound A was dissolved in 100 ml. of 2 N NaOH. Zinc dust (30 g.) and sodium hydroxide (50 ml. of a 25% solution) were added slowly to the well-stirred solution. The mixture was then cooled to <30° C. and acidified with concentrated hydrochloric acid. After stirring for 2 hours, the precipitate was filtered. Compound B was recrystallized from toluene (m.p. 185°–188° C., 60% yield). A mixture of the sodium salt of Compound B (0.01 mole) and 4-bromomethylbenzylidenemalononitrile (0.01 mole) in 250 ml. of ethanol was refluxed for 15 hours. The product, C, was crystallized from methyl cellosolve after removal of sodium bromide by filtration. (Yield: 65%).

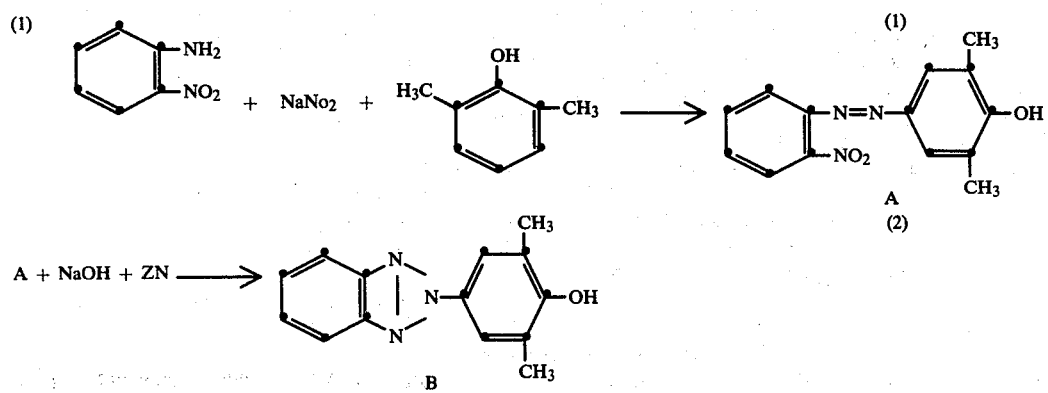

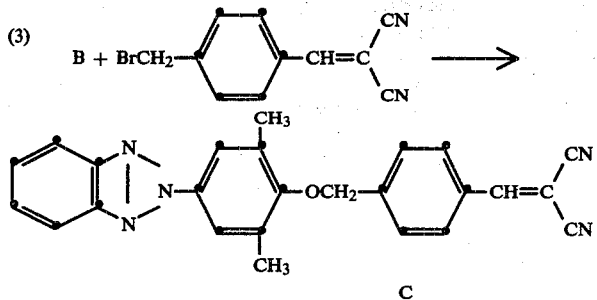

Other novel bichromophoric compounds can be prepared by substitution of other benzotriazoles for 4-(2H-benzotriazol-2-yl)-2,6-dimethylphenol, such as 4-(5-chloro-2H-benzotriazol-2-yl)-2,6-dimethylphenol, 4-(5-chloro-2H-benzotriazol-2-yl)phenol, 4-(5-methyl-2H-benzotriazol-2-yl)-2,6-dimethylphenol, 4-(5-methyl-2H-benzotriazol-2-yl)-2-methylphenol, 4-(5-chloro-2H-benzotriazol-2-yl)-2-methylphenol, 4-(2H-benzotriazol-2-yl)-2-methylphenol, 4-(2H-benzotriazol-2-yl)-2-chlorophenol, 4-(5-chloro-2H-benzotriazol-2-yl)-2-chlorophenol, 4-(5-methyl-2H-benzotriazol-2-yl)-2-chlorophenol, 4-(2H-benzotriazol-2-yl)-2,6-dimethoxyphenol, 4-(5-chloro-2H-benzotriazol-2-yl)-2,6-dimethoxyphenol, 4-(5-methyl-2H-benzotriazol-2-yl)-2,6-dimethoxyphenol, 4-(2H-benzotriazol-2-yl)-2-methoxyphenol, 4-(5-chloro-2H-benzotriazol-2-yl)-2-methoxyphenol, and 4-(5-methyl-2H-benzotriazol-2-yl)-2-methoxyphenol.

Also, other bichromophoric compounds can be prepared by substituting other styrene compounds such as 4-(β,β-dicarbomethoxyvinyl)benzyl bromide, 4-[β,β-dicarbo(2-ethylhexyloxy)vinyl]phenyl ethyl bromide, 4-[β,β-dicarbo(n-dodecyloxy)vinyl]phenoxy ethyl bromide, 2-chloro-4-(β,β-dicarbomethoxyvinyl)benzyl bromide, 2-methyl-4-(β,β-dicarbo-n-butoxyvinyl)benzyl bromide, 2-methoxy-4-(β,β-dicarbo-n-butoxyvinyl)benzyl bromide, 2-acetamido-4-(β,β-dicarboethoxyvinyl)benzyl bromide, 2-phenyl-4-[β,β-dicarbo(2-hydroxyethoxy)vinyl]benzyl bromide, 2-cyclohexyl-4-[β,β-dicarbo(2-methoxyethoxy)vinyl]benzoyl bromide, 2-bromo-4-[β,β-dicarbo(2-n-butoxyethoxy)vinyl]benzyl bromide, 2-cyano-4-(β,β-dicarbo-n-dodecyloxyvinyl)butyl bromide, 2-isopropyl-4-(β,β-dicarbomethoxyvinyl)methyl bromide, 2-n-butyl-4-[β,β-dicarbo(2-β-methoxyethoxy)vinyl]benzyl bromide, 2-t-amyl-4-(β,β-dicarbo-isopropyloxyvinyl)ether bromide, 4-(β,β-dicyanovinyl)benzyl bromide, 2-methyl-4-(β,β-dicyanovinyl)benzyl bromide, 2-cyano-4-(β,β-dicyanovinyl)benzyl bromide, 2-t-butyl-4-(β,β-dicyanovinyl)benzyl bromide, 2-n-cyclohexyl-4-(β,β-dicyanovinyl)ethyl bromide, 2-t-octyl-4-(β,β-dicyanovinyl)benzyl bromide, 2-benzamido-4-(β,β-dicyanovinyl)benzyl bromide, 2-n-dodecyloxy-4-(β,β-dicyanovinyl)benzyl bromide, 4-(β-cyano-β-carbomethoxyvinyl)benzyl bromide, 2-cyclo-pentyl-4-(β-cyano-β-carboethoxyvinyl)benzyl bromide, 2-isopropyl-4-[β-cyano-β-carbo(2-ethylhexyloxy)vinyl]benzyl bromide, 2-chloro-4-[β-cyano-β-carbo(2-methoxyethoxy)vinyl]benzyl bromide, 2-methoxy-4-(β-cyano-β-carbomethoxyvinyl)benzyl bromide, for 4-bromomethyl benzylidene malononitrile.

The example hereinabove shows the linking group as an oxyalkyleneoxy group. Other linking groups can be provided as known in the art, as for example:

1. an oxycarbonylalkyleneoxy by esterification of an acid or acid chloride with an alcohol or phenol in alkaline medium;
2. an oxycarbonyloxy by the reaction of phosgene with alcohol or phenol in alkaline medium;
3. an alkyleneoxy by the reaction of halide with alkali salt of alcohol or phenol;
4. an alkyleneoxyalkyleneoxy by the reaction of halide with alkali salt of alcohol or phenol;
5. a sulfinyldioxy by the reaction of thionyl chloride with alcohol or phenol in alkaline solution;
6. a thio by the reaction of a sodium sulfide with a halide;
7. an oxy(alkoxy)phosphinooxy by the reaction of a dichlorophosphite with phenol in the presence of a base;
8. an N-alkyl or N-arylaminocarbonyl by the reaction of an acid chloride with an amine;
9. an N-alkyl or N-arylaminocarbonylalkoxy by the reaction of an acid chloride with an amine;
10. an N-alkyl or N-arylaminocarbonylamino by the reaction of phosgene with an amine;
11. an N-alkyl or N-arylaminoalkylene by the reaction of an alkyl halide with an amine;
12. an N-alkyl or N-arylaminoalkyleneoxy by the reaction of an oxyalkyl halide with an amine.

These bichromophoric benzotriazole-styrene compositions find particular utility as ultraviolet stabilizers in organic compositions requiring ultraviolet stability. Such compositions include polymeric compositions such as, for example, polyester fiber and molding compositions, poly-alpha-olefins, polyamides, acrylics, fluorocarbon resins, cellulose esters and the like, as well as molded or shaped articles, film and coatings formed from such materials and the like. Such compositions also include natural and synthetic rubbers, such as natural rubber, as well as organic materials such as oils, fats, and unsaturated organic materials and materials having such materials contained therein such as paints, varnishes, cosmetics and the like.

The invention has been described in detail with particular reference to preferred embodiments thereof, but it will be understood that variations and modifications can be effected within the spirit and scope of the invention.

We claim:
1. A compound having the formula:
 A—B—C wherein A is a group having the structure

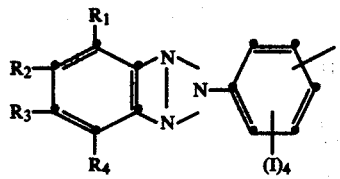

wherein

R₁, R₂, R₃ and R₄ are hydrogen, chloro, bromo, lower alkyl having 1 to 12 carbon atoms, cyclohexyl, phenyl, lower alkylphenyl, phenyl-substituted-phenyl, alkoxy, cyano, carboalkoxy, acetamido and the substituents R₁ and R₂, R₂ and R₃, and R₃ and R₄, combined with the carbon atoms to which they are attached, are joined alkylene groups completing a carbocyclic ring, which ring can also be substituted with one or more of the substituents listed above for R₁, R₂, R₃ and R₄;

I is the same as R₁, R₂, R₃ and R₄ and is present on all positions of the benzenoid ring, except the carbon atom attached to the heterocyclic ring and the carbon atom attached to the B group connecting the heterocyclic aromatic A group with the aromatic C group, wherein B is a linking group connecting A and C and is carbonyloxy, oxycarbonylalkyleneoxy, alkyleneoxycarbonyloxy, oxyalkylenecarbonyloxy, oxycarbonyloxy, alkyleneoxy, alkyleneoxyalkyleneoxy, oxyalkylene phenylenealkyleneoxy, thio, thioalkyleneoxy, sulfinyldioxy, oxy(alkoxy)phosphinooxy, carbonylamino, N-alkylcarbonylamino, N-phenylcarbonylamino, aminocarbonylalkyleneoxy, N-alkylaminocarbonylalkyleneoxy, N-phenylaminocarbonylalkyleneoxy, aminocarbonylamino, N-alkylaminocarbonylamino, N-alkylamino, N-phenylamino, N-alkylaminoalkyleneoxy, N-phenylaminoalkyleneoxy, oxyalkyleneoxy, oxyphenyleneoxy, oxy; and wherein C is a group having the formula

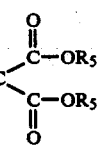 1.

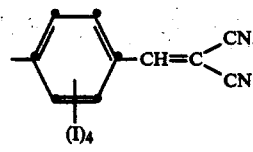 2

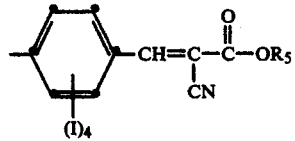 3.

wherein I is the same substituent as listed above and is present in all positions of the benzenoid rings except the carbon atom attached to the B group connecting the A and C moieties, and said I substituents can all be one of the substituents listed above or different listed substituents and R₅ is an alkyl group containing 1 to 20 carbon atoms or a hydroxyalkyl group or an alkoxyalkyl group containing 1 to 20 carbon atoms.

2. A compound according to claim 1 wherein said B linking group is carbonyloxy.

3. A compound according to claim 1 wherein said B linking group is oxycarbonylalkyleneoxy.

4. A compound according to claim 1 wherein said B linking group is alkyleneoxycarbonyloxy.

5. A compound according to claim 1 wherein said B linking group is oxyalkylenecarbonyloxy.

6. A compound according to claim 1 wherein said B linking group is oxycarbonyloxy.

7. A compound according to claim 1 wherein said B linking group is alkyleneoxy.

8. A compound according to claim 1 wherein said B linking group is alkyleneoxyalkyleneoxy.

9. A compound according to claim 1 wherein said B linking group is oxyalkylenearylenealkyleneoxy.

10. A compound according to claim 1 wherein said B linking group is thio.

11. A compound according to claim 1 wherein said B linking group is thioalkyleneoxy.

12. A compound according to claim 1 wherein said B linking group is sulfinyldioxy.

13. A compound according to claim 1 wherein said B linking group is oxy(alkoxy)phosphinooxy.

14. A compound according to claim 1 wherein said B linking group is carbonylamino.

15. A compound according to claim 1 wherein said B linking group is N-alkylcarbonylamino.

16. A compound according to claim 1 wherein said B linking group is N-arylcarbonylamino.

17. A compound according to claim 1 wherein said B linking group is aminocarbonylalkyleneoxy.

18. A compound according to claim 1 wherein said B linking group is N-alkylaminocarbonylalkyleneoxy.

19. A compound according to claim 1 wherein said B linking group is N-arylaminocarbonylalkyleneoxy.

20. A compound according to claim 1 wherein said B linking group is aminocarbonylamino.

21. A compound according to claim 1 wherein said B linking group is N-alkylaminocarbonylamino.

22. A compound according to claim 1 wherein said B linking group is N-alkylamino.

23. A compound according to claim 1 wherein said B linking group is N-arylamino.

24. A compound according to claim 1 wherein said B linking group is N-alkylaminoalkyleneoxy.

25. A compound according to claim 1 wherein said B linking group is N-arylaminoalkyleneoxy.

26. A compound according to claim 1 wherein said B linking group is oxyalkyleneoxy.

27. A compound according to claim 1 wherein said B linking group is oxyaryleneoxy.

28. A compound according to claim 1 having the formula:

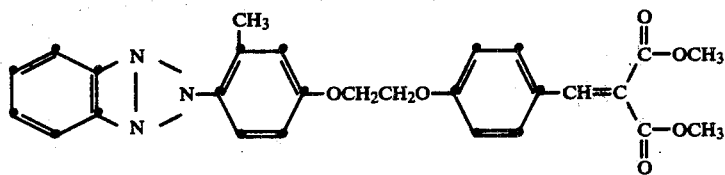
29. A compound according to claim 1 having the formula:
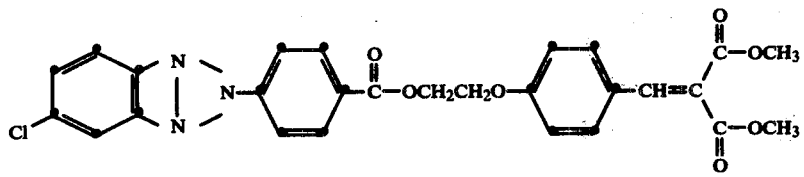
30. A compound according to claim 1 having the formula:
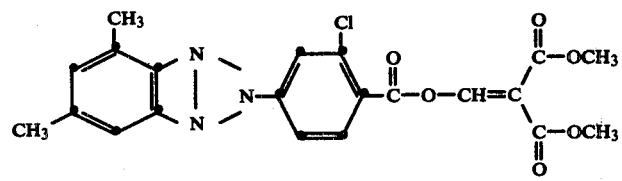
31. A compound according to claim 1 having the formula:
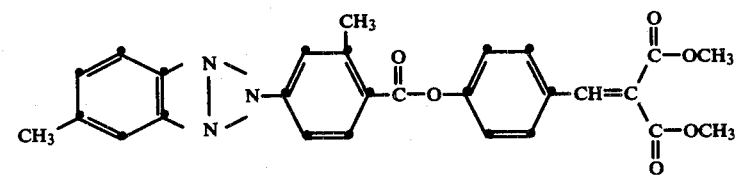
32. A compound according to claim 1 having the formula:
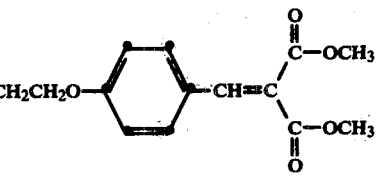
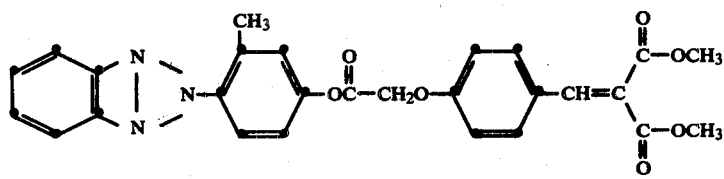
33. A compound according to claim 1 having the formula:
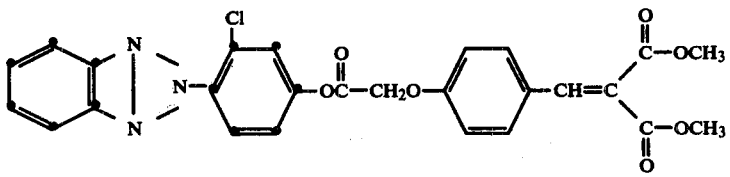
34. A compound according to claim 1 having the formula:

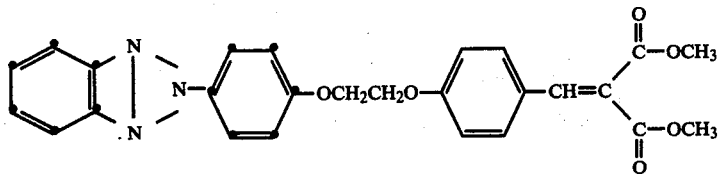
35. A compound according to claim 1 having the formula:
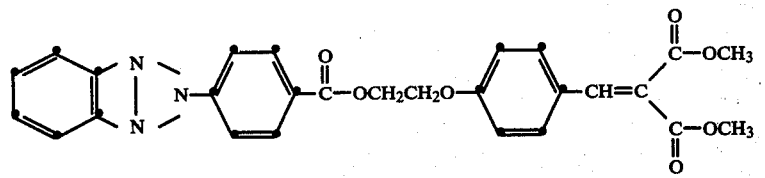
36. A compound according to claim 1 having the formula:
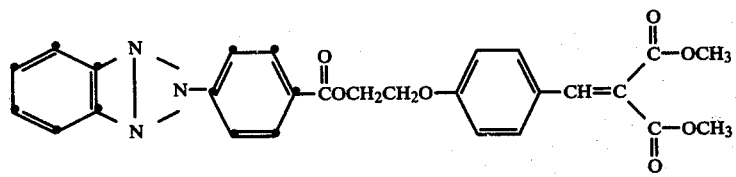
37. A compound according to claim 1 having the formula:
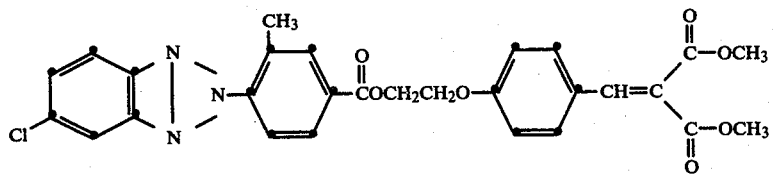
38. A compound according to claim 1 having compound has the formula:
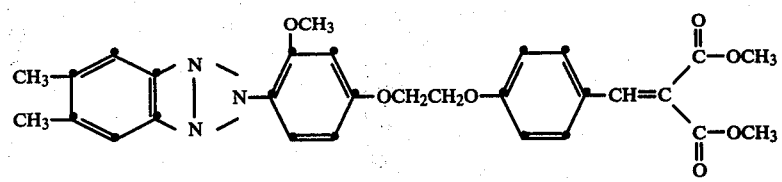
39. A compound according to claim 1 having the formula:
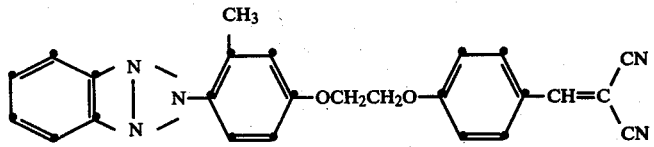
40. A compound according to claim 1 having the formula:
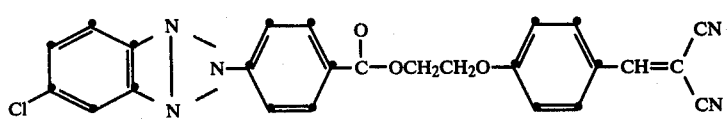
41. A compound according to claim 1 having the formula:

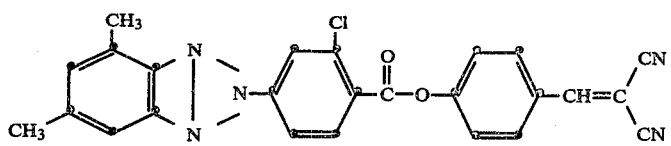
42. A compound according to claim 1 having the formula:
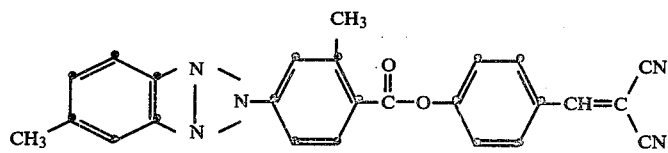
43. A compound according to claim 1 having the formula:
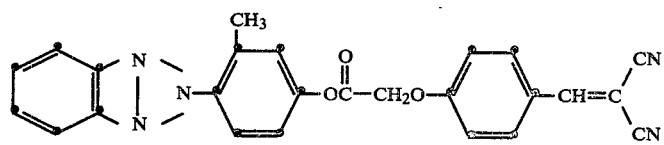
44. A compound according to claim 1 having the formula:
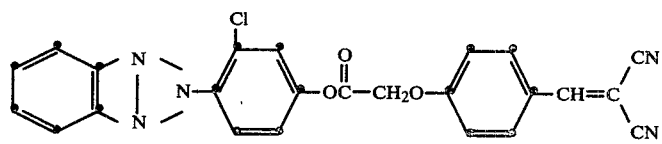
45. A compound according to claim 1 having the formula:
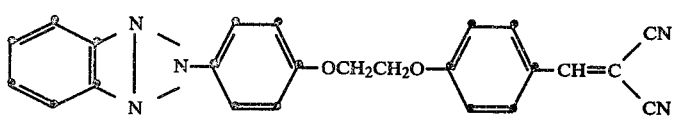
46. A compound according to claim 1 having the formula:
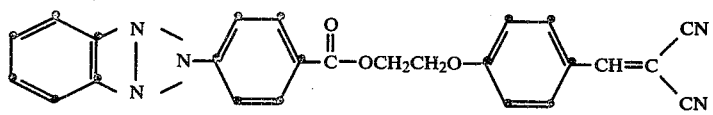
47. A compound according to claim 1 having the formula:
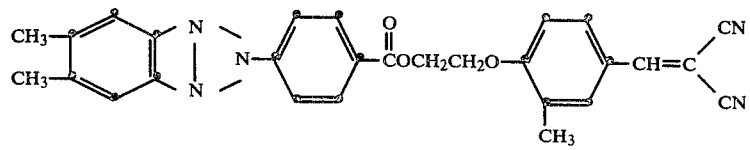
48. A compound according to claim 1 having the formula:

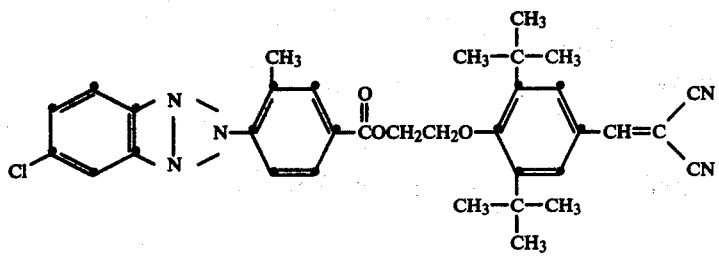

49. A compound according to claim 1 wherein said bichromophoric compound has the formula:

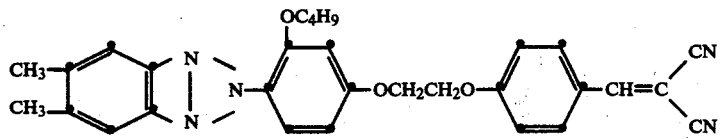

50. A compound according to claim 1 having the formula:

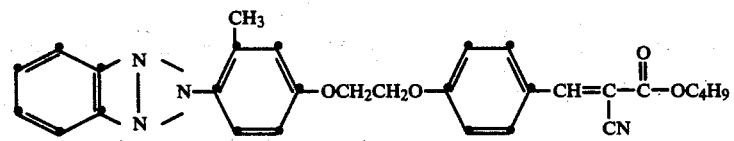

51. A compound according to claim 1 having the formula:

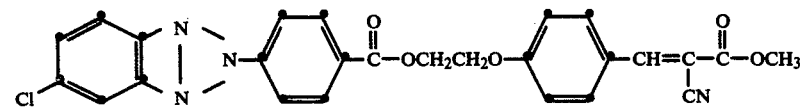

52. A compound according to claim 1 having the formula:

53. A compound according to claim 1 having the formula:

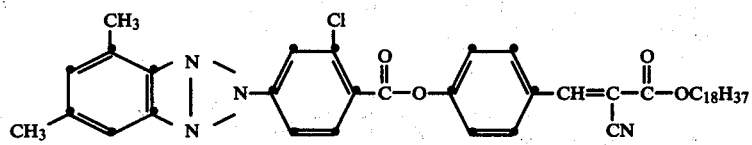

54. A compound according to claim 1 having the formula:

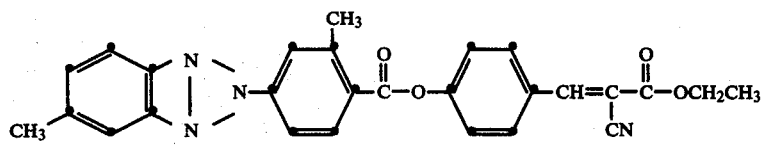

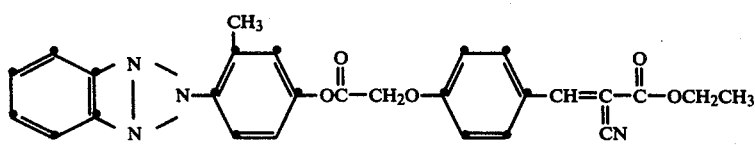

55. A compound according to claim 1 having the formula:

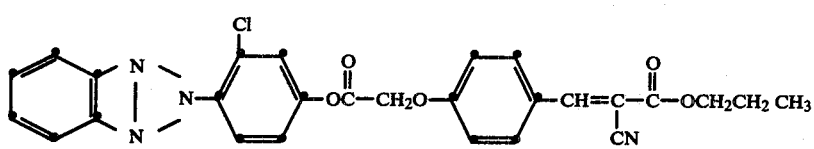
56. A compound according to claim 1 having the formula:
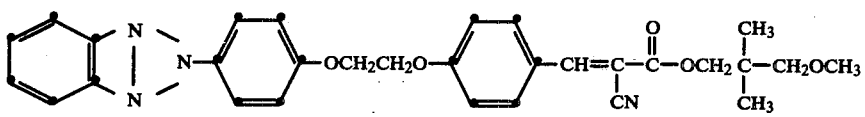
57. A compound according to claim 1 having the formula:
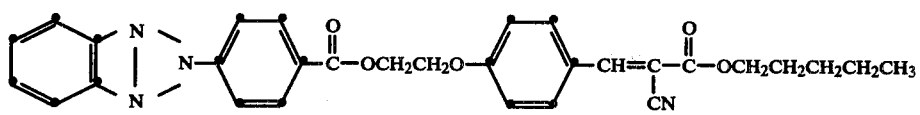
58. A compound according to claim 1 having the formula:
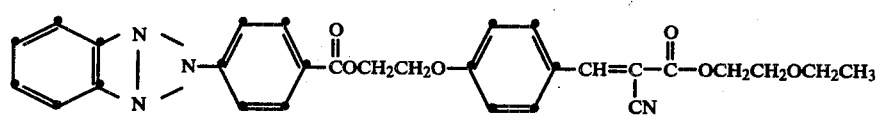
59. A compound according to claim 1 having the formula:
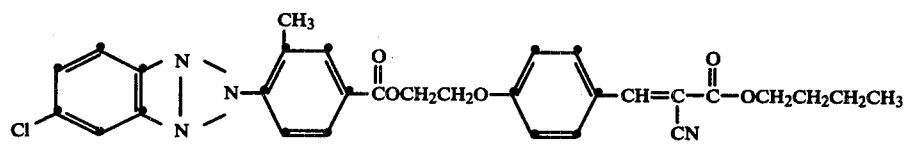
60. A compound according to claim 1 having the formula:
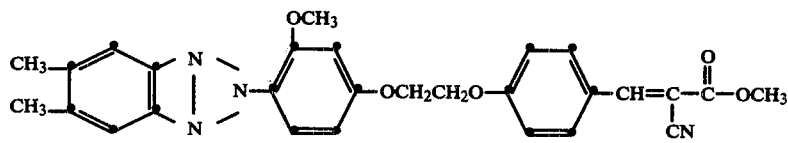
* * * * *

UNITED STATES PATENT AND TRADEMARK OFFICE
CERTIFICATE OF CORRECTION

PATENT NO. : 4,159,270
DATED : June 26, 1979
INVENTOR(S) : Gether Irick, Jr. et al It is certified that error appears in the above-identified patent and that said Letters Patent are hereby corrected as shown below:

Column 11, the formula of Claim 30 should read

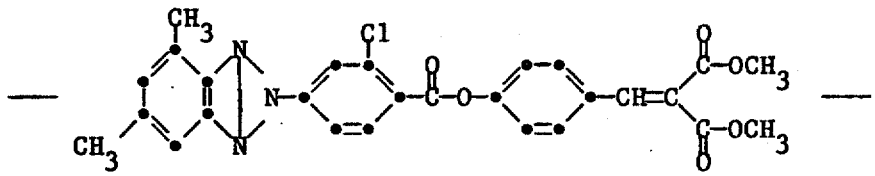

Column 14, the first two lines of Claim 38 should read

—38. A compound according to Claim 1 having the formula:—

Column 17, the first two lines of Claim 49 should read

—49. A compound according to Claim 1 having the formula:—

Column 18, the formula of Claim 54 should read

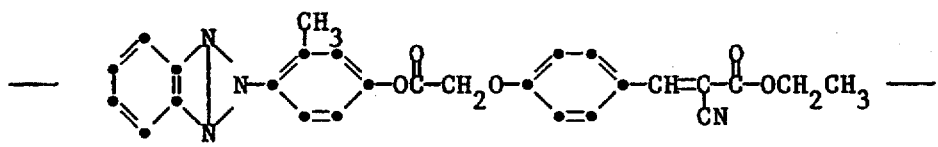

Signed and Sealed this

Twenty-third Day of October 1979

[SEAL]

Attest:

RUTH C. MASON
Attesting Officer

LUTRELLE F. PARKER
Acting Commissioner of Patents and Trademarks